United States Patent [19]

Rensi

[11] Patent Number: 5,284,962

[45] Date of Patent: Feb. 8, 1994

[54] MULTISTAGE PROCESS FOR MAKING METHYL CARBAMATES

[75] Inventor: Terence A. Rensi, Hockessin, Del.

[73] Assignee: E. I. Du Pont de Nemours and Company, Wilmington, Del.

[21] Appl. No.: 958,629

[22] Filed: Oct. 9, 1992

[51] Int. Cl.⁵ .......................................... C07D 317/64
[52] U.S. Cl. .................................. 549/438; 549/452; 549/467; 564/255; 564/342; 564/343
[58] Field of Search ....................... 549/438, 452, 467; 564/255, 342, 343

[56] References Cited

U.S. PATENT DOCUMENTS

| | | | |
|---|---|---|---|
| 3,506,698 | 4/1970 | Jelinek | 558/3 |
| 3,832,400 | 8/1974 | Meyer et al. | 564/255 |
| 4,086,246 | 4/1978 | Toth et al. | |
| 4,278,807 | 7/1981 | Boros et al. | |
| 4,659,845 | 4/1987 | Rivetti et al. | |
| 4,668,806 | 5/1987 | Mrowca | 564/255 |
| 4,698,438 | 10/1987 | Blaisdell et al. | 549/438 |
| 5,021,590 | 6/1991 | Mizia et al. | 549/438 |

Primary Examiner—Marianne M. Cintins
Assistant Examiner—John Peabody
Attorney, Agent, or Firm—James A. Costello

[57] ABSTRACT

A continuous process employing at least two reaction stages for manufacturing pesticides from methyl isocyanate and oxime or phenol reactants in water.

12 Claims, No Drawings

MULTISTAGE PROCESS FOR MAKING METHYL CARBAMATES

This invention pertains to a multistage process for preparing methyl carbamates. U.S. Pat. No. 4,698,438 discloses a process for manufacturing pesticides from methyl isocyanate (MIC) in an organic solvent. U.S. Pat. No. 3,506,698 discloses a single stage process for making certain N-methylcarbamates by contacting an oxime with MIC in an aqueous reaction medium.

SUMMARY OF THE INVENTION

This invention concerns a continuous process for manufacturing N-methylcarbamate pesticides by reacting an oxime or phenol with methyl isocyanate supplied to the reaction in a vapor phase, the oxime or phenol being selected from the group

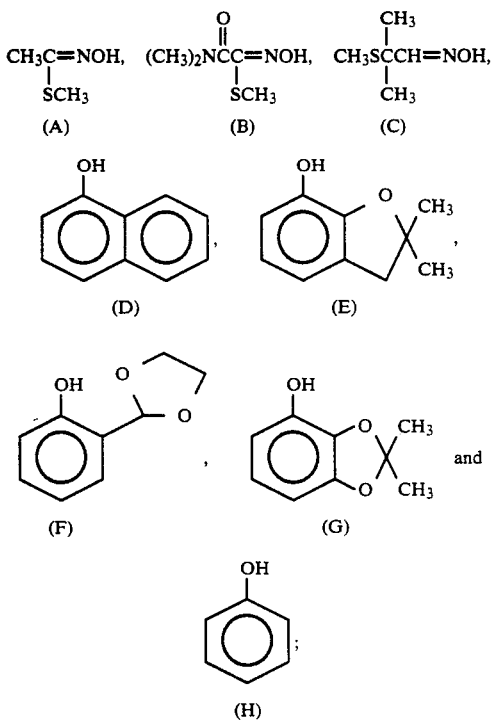

wherein the improvement comprises:
(i) conducting the reaction in water in the substantial absence of an organic solvent;
(ii) cocurrently introducing the reactants into a multiply staged reactor system;
(iii) attenuating the amount of methyl isocyanate available for reaction with the oxime or phenol in the first reactor stage, said methyl isocyanate being supplied as a vapor in a diluent gas,
(iv) transferring reactants into a subsequent reactor stage before the reaction is complete, thereby minimizing formation of by-product dimethylurea; and
(v) completing the reaction in the second or subsequent stage of the reactor.

DETAILS OF THE INVENTION

MIC gas can be generated directly from MIC or by oxidative dehydrogenation of monomethylformamide (MMF) as taught in U.S. Pat. No. 4,537,726. The oxime and phenol reactants are known. The process is typically carried out by continuously feeding MIC, as a vapor in a diluent gas such as nitrogen, and the oxime (or phenol) in water, cocurrently, to a staged reactor system. The reactor system consists of two or more reaction vessels or stages connected in series. A sieve tray reactor can be employed in the process of this invention. The two reactant feeds are simultaneously introduced to the first vessel or stage of the reactor system wherein the reaction is controlled to allow not more than about 95% conversion of the oxime (or phenol) to product. This control will minimize the formation of dimethylurea (DMU). Preferred conversion range is 20% to 90%.

Control of the oxime (or phenol) conversion in the first vessel or stage is typically accomplished by controlling MIC absorption or by splitting the MIC feed and adding it directly to a later stage. In a reactor system consisting of linked vessels, MIC absorption can be controlled by adjusting agitator speed (mixing efficiency) or liquid level. The partially reacted liquid stream and the MIC-containing vent stream from the first stage are then both fed to a second stage and the reaction is completed to the desired conversion. The oxime (or phenol) concentration in the final stage is controlled at about 0.2 to 2 weight percent to minimize dimethylurea (DMU) formation. This is accomplished by controlling the MIC to oxime (or phenol) ratio and/or MIC absorption. DMU is a contaminant from the reaction of MIC with water.

A basic catalyst such as triethylamine (TEA) or the like can be added to the oxime (phenol)/water mixture to decrease reaction time and improve selectivity. In general, the reaction is carried out between 0°-100° C., preferably between 20°-60° C. The reaction vessels are typically equipped for external heating/cooling, agitation and material transfer.

Cocurrent feeding of reactant streams containing MIC and oxime (or phenol) to a single vessel or first stage of multi-taged reactor such as a sieve tray reactor, employing water as a solvent, and completion of the reaction in a subsequent vessel or second or subsequent stage of a multi-stage reactor yields high conversions to methylcarbamate products with low contamination by DMU and unreacted starting materials. The staged nature of the process also permits efficient removal of MIC from the vapor stream, thereby improving process yields. The present invention offers several advantages for commercial scale production. A continuous process allows close-coupling with the MIC production process which minimizes or eliminates the need to store highly toxic liquid MIC. Safety is enhanced by eliminating the need for an organic solvent which is often toxic and/or flammable. Use of water as the solvent eliminates organic solvent emissions and discharges to the environment. The ability to achieve high oxime/phenol conversions with relatively low DMU formation simplifies product isolation, eliminates the need to recover and recycle unconverted oxime/phenol, and improves product purity.

EXAMPLE 1

A two-stage, cocurrently fed, continuous reactor system was used to react MIC and the oxime, S-methyl N-hydroxyethanimidothioate, to produce S-methyl N-[[(methylamino)carbonyl]oxy]ethanimidothioate (methomyl). The reactor system consisted of two 500-mL, baffled, agitated, jacketed resin kettles operated in series. MIC was fed as an MIC/nitrogen vapor stream and was introduced to the first reactor through a dip tube/sparge-ring arrangement. The oxime was fed to the first reactor as a slurry in water. Conversion of the oxime in the first reactor was controlled by adjusting the reactor level and/or agitation rate. The vent stream from the first reactor was fed to the second reactor through a dip tube/sparge-ring arrangement. The partially converted product from the first reactor was fed to the second reactor at a rate to maintain a constant level in the first reactor. Conversion of oxime in the second reactor was controlled by adjusting the MIC to starting material ratio. The product solution was continuously removed from the second reactor at a rate to maintain a constant level. Water was circulated through the reactor jackets to maintain a temperature of 51° C. The off-gas from the second reactor was vented to a caustic scrubber to destroy the unreacted MIC.

During steady state operation, MIC was fed at a rate of 1.2 g/min and vaporized and mixed with nitrogen which was fed at a rate of approximately 2200 mL/min. The oxime was fed at a rate of 4.9 g/min as a 40% slurry in water containing 0.1% triethylamine (TEA). Conversion of the oxime in the first reactor was about 85%. The composition of the product solution from the second reactor was approximately 48% product, 1.2% oxime and 1.7% DMU. This composition corresponded to 96% conversion of the oxime and about 9% of the original MIC as DMU. The vent steam from the second reactor contained about 0.7% MIC corresponding to removal of greater than 98% from the gas stream.

EXAMPLE 2

The staged reactor system described in Example 1 was used to react MIC and the oxime, methyl 2-(dimethylamino)-N-hydroxy-2-oxoethanimidothioate, to produce methyl 2-(dimethylamino)-N-[[(methylamino)carbonyl]oxy]-2-oxoethanimidothioate (oxamyl). The reactors were maintained at approximately 42° C. During steady state operation, MIC was fed at a rate of 1.2 g/min and vaporized and mixed with nitrogen which was fed at approximately 2200 mL/min. The oxime was fed at a rate of 7.9 g/min as a 40% slurry in water containing 0.2% TEA. Conversion of the oxime in the first reactor was about 93%. The composition of the product solution from the second reactor was approximately 47% title product, 0.9% oxime and 0.8% DMU. This composition corresponded to 97% conversion of the oxime and 8% of the original MIC as DMU. The vent stream from the second reactor contained about 0.2% MIC corresponding to removal of greater than 99% from the gas stream.

EXAMPLES 3 TO 8

By the general procedures of Examples 1 and 2, the oxime/phenols of Column 2 of Table 1 can be reacted with MIC to prepare the carbamates of Column 3.

TABLE 1

| Example No. | Oxime/Phenol Reactant | Carbamate Product |
|---|---|---|
| 3 | 2-methyl-2-(methylthio)propanol oxime (C) | aldicarb |
| 4 | α-naphthol (D) | carbaryl |
| 5 | 2,3-dihydro-2,2-dimethyl-7-hydroxybenzofuran (E) | carbofuran |
| 6 | 2-(1,3-dixolan-1-yl)phenol (F) | N-methylcarbamoyloxy-2-(1,3-dioxolan-1-yl)benzene |
| 7 | 2,2-dimethyl-1,3-benzodioxol-4-ol (G) | bendiocarb |
| 8 | phenol (H) | phenyl methylcarbamate |

I claim:

1. An improved continuous process for forming an N-methyl carbamate pesticide by reacting an oxime or phenol with methyl isocyanate, the oxime or phenol being selected from the group consisting of:

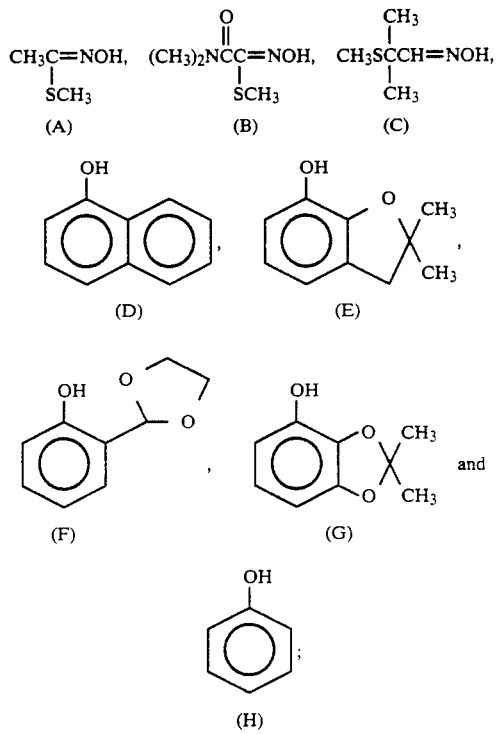

wherein the improvement comprises:
   (i) conducting the reaction in water in the substantial absence of an organic solvent;
   (ii) cocurrently introducing the reactants into a multiply staged reactor system;
   (iii) attenuating the amount of methyl isocyanate available for reaction with the oxime or phenol in the first reactor stage, said methyl isocyanate being supplied as a vapor in a diluent gas,
   (iv) transferring the reactants into a subsequent reactor stage before the reaction is complete, thereby minimizing formation of byproduct dimethylurea; and
   (v) completing the reaction in the second or subsequent stage of the reactor.

2. A method according to claim 1 wherein the staged reactor system comprises two reactors in series.

3. A method according to claim 1 wherein the staged reactor system comprises a column reactor.

4. A method according to claim 3 wherein the column reactor is a sieve tray reactor.

5. A method according to claim 1 wherein the oxime is A.

6. A method according to claim 1 wherein the oxime is B.

7. A method according to claim 1 wherein the phenol is C.

8. A method according to claim 1 wherein the phenol is D.

9. A method according to claim 1 wherein the phenol is E.

10. A method according to claim 1 wherein the phenol is F.

11. A method according to claim 1 wherein the phenol is G.

12. A method according to claim 1 wherein the phenol is H.

* * * * *